United States Patent [19]
Sanghera et al.

[11] Patent Number: 5,525,800
[45] Date of Patent: Jun. 11, 1996

[54] SELECTIVE MULTI-CHEMICAL FIBER OPTIC SENSOR

[75] Inventors: Jasbinder S. Sanghera, Greenbelt, Md.; Pablo C. Pureza, Burke, Va.; Ishwar D. Aggarwal, Fairfax Station, Va.; Gregory Nau, Alexandria, Va.

[73] Assignee: The United States of America as represented by the Secretary of the Navy, Washington, D.C.

[21] Appl. No.: 332,294

[22] Filed: Oct. 31, 1994

[51] Int. Cl.$^6$ ................................... G01N 21/17
[52] U.S. Cl. ................ 250/339.08; 250/339.07; 250/227.25
[58] Field of Search ............... 250/339.08, 339.07, 250/339.09, 227.25

[56] References Cited

U.S. PATENT DOCUMENTS 5,239,176  8/1993  Stevenson ................. 250/227.25

OTHER PUBLICATIONS

Krska et al., "New IR Fiber–Optic Chemical Sensor For In Situ Measurements Of Chlorinated Hydrocarbons In Water," Applied Spectroscopy, vol. 47, No. 9, 1993, pp. 1484–1487.

Heo et al., "Remote Fiber–Optic Chemical Sensing Using Evanescent-Wave Interactions In Chalcogenide Glas Fibers '" Applied Optics, vol. 30, No. 27, 20 Sept. 1991, pp. 3944–3951.

Primary Examiner—Davis L. Willis
Assistant Examiner—Richard Hanig
Attorney, Agent, or Firm—Thomas E. McDonnell; George A. Kap

[57] ABSTRACT

A fiber optic sensor for detecting at least one chemical by evanescent wave spectroscopy comprises a generator of a light signal, a mirror for introducing the light signal into a fiber, a clad optical chalcogenide glass fiber, a mirror for directing the light signal from the fiber into a detector, and a detector for detecting chemicals by the fiber. The fiber comprises a core and a clad having lower refractive index than the core enveloping and being in continuous contact with the core, at least one region on the fiber completely or partially devoid of the clad, and a polymer disposed in the region having affinity for the chemical(s). There being a different polymer in each region if there is more than one region.

20 Claims, 4 Drawing Sheets

SELECTIVE MULTI-CHEMICAL FIBER OPTIC SENSOR

FIELD OF INVENTION

This invention pertains to fiber optic sensors, and more particularly to chalcogenide fiber optic sensors including at least one chemical in an aqueous medium.

BACKGROUND OF INVENTION

Over the years, an increasing number of environmental sites have been characterized and determined to be polluted with hazardous and toxic chemicals such as halogenated hydrocarbons, benzene, toluene, and xylene. These chemicals pose serious problems to the ecology, especially if they get into drinking water. Therefore, there is an urgent need to identify the location and concentration of such hazardous chemicals.

The identification of chemicals has relied heavily on removal of the chemical samples from a contaminated site and subsequent analysis of the samples using techniques such as gas chromatography and/or mass spectroscopy. These techniques are inherently costly, slow, time consuming, and do not give real time analysis since the chemicals are volatile and their concentrations decrease with time. Hence, the techniques heretofore employed do not give reliable information.

Alternative detection techniques have been utilized based on infrared (IR) fiber optic technology. Silica-based fiber optics is a well-developed technology that has had a major impact on telecommunications, medicine, and industry. Optical fibers fabricated with silica-based glass have achieved the intrinsic attenuation limit of 0.2 dB/km at 1.5 μm. Widespread production of optical fibers from silica-based glasses proves their dominant role in communications for both voice and data; in optical and electro-optical systems in a myriad of fields; and in sensors for medicine, industry, and the military.

The halide glasses are of interest in high energy laser applications because of their low linear and non-linear refractive indices and low dispersion, but are unsuitable for practical handling and use because of their hygroscopicity. Certain halide glasses transmit further in the IR than silica glasses and have potential applications as ultra-low loss fibers but are prone to devitrification and thus cannot be drawn into crystal-free fibers. The heavy metal fluoride glasses exhibit a lesser tendency toward crystallization and higher IR transparency.

Most chemicals possess characteristic vibrational bands in the IR region between about 2–12 micrometers or microns. The chemicals referred to herein include halogenated hydrocarbons, benzene, toluene, and xylene. Since silica-based fibers transmit in the region of up to about 2 μm and halide fibers transmit in the region of up to about 3 μm, it should be apparent that these prior art fibers are incapable of detecting the various chemicals that one may want to detect.

The article by Krska et al. in vol. 47, No. 7, pp. 1484–1487 of the 1993 journal *Applied Spectroscopy* entitled "The New IR Fiber-Optic Chemical Sensor for in Situ Measurements of Chlorinated Hydrocarbons in Water" discloses an unclad crystalline fiber of silver halide for detecting chlorinated hydrocarbons in water. A low density polyethylene deposited on the fiber concentrates the chlorinated hydrocarbons to facilitate their detection by evanescent wave spectroscopy. Another article by Heo et al in vol. 30, No. 27, dated Sep. 20, 1991, in *Applied Optics*, entitled "Remote fiber-optic chemical sensing using evanescent-wave interactions in chalcogenide glass fibers" discloses detection of analytes with an unclad chalcogenide fiber.

OBJECTS OF INVENTION

It is an object of this invention to provide a clad optic fiber for the real time detection of chemicals having absorption bands in the wavelength of about 2–12 microns.

It is another object of this invention to provide a chalcogenide optic fiber comprising a core and a clad surrounding the core, the fiber having at least one region devoid of the clad provided with a polymer coating.

It is another object of this invention to provide a non-crystalline chalcogenide optical fiber sensor for detecting chemicals at a level below parts per million.

It is another object of this invention to provide a chalcogenide optic fiber having an attenuation below 0.2 dB/km.

These and other objects of this invention are attained by a fiber optic sensor which is a clad chalcogenide glass fiber which transmits light in the wavelength range of about 2–12 μm and which has regions devoid of the clad coated with different polymeric materials which have the capacity to concentrate chemicals to be tested for presence and/or concentration thereof.

DETAILED DESCRIPTION OF INVENTION

Figure 1:
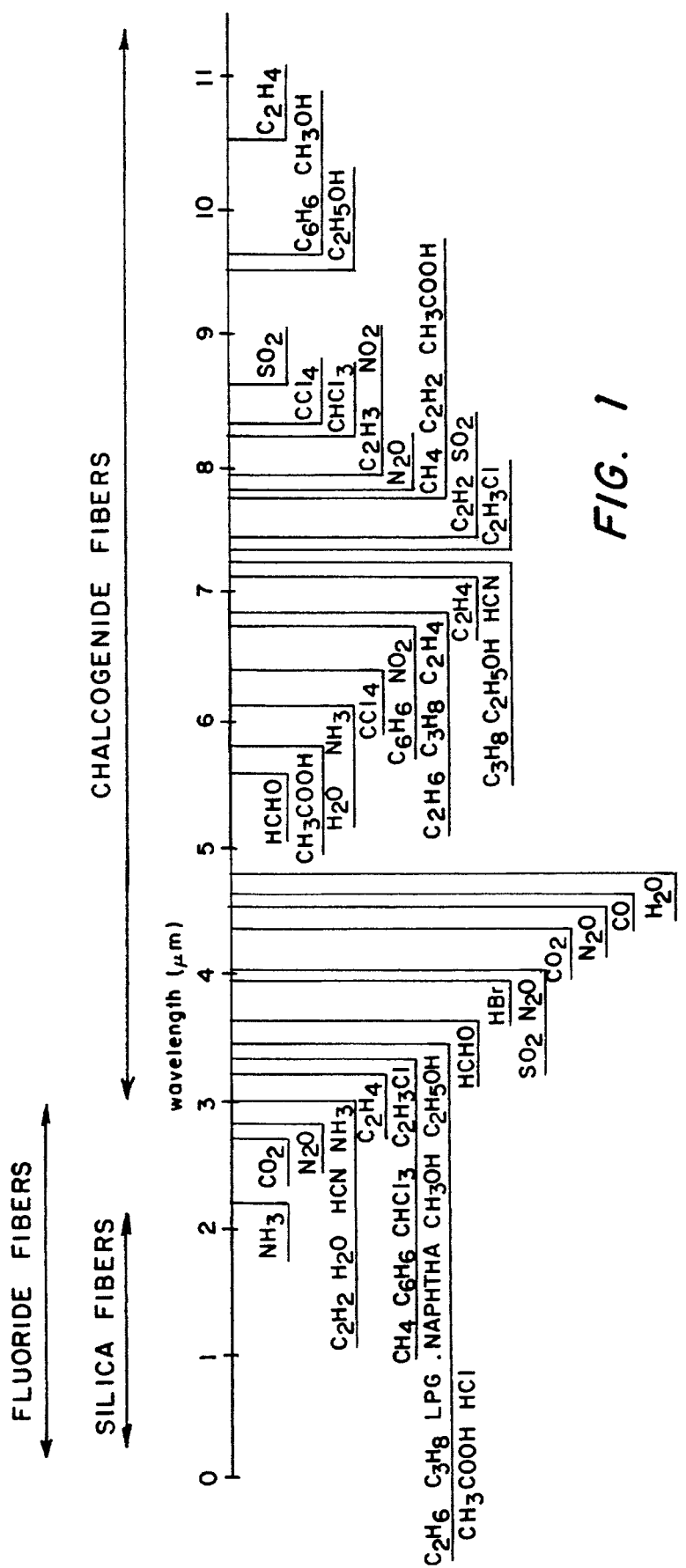
FIG. 1 shows the vibrational bands of a limited number of chemicals over the wavelength range of 0–12 μm and the transmittance of silica, fluoride and chalcogenide fibers.

This invention pertains to the detection of at least one chemical by a chalcogenide optic glass fiber sensor having a core and a clad surrounding the core except at an unclad region. The unclad region is coated with a polymer that specifically interacts with at least one of the chemicals.

The glass fiber used in the sensor of this invention can be of any cross-sectional shape. Typically, however, the fiber is circular in cross-section. In the present specification, the fiber is described with reference to a circular cross-section. Those of ordinary skill in the art can extrapolate that description when producing fiber having other cross-sectional shapes. The fiber in the sensor can be of any length desired and is about 20–500 microns in diameter, taking into account only core and clad surrounding the core. The core is about 10–90%, preferably 30–70% of the fiber diameter, with remainder being the clad. In order to keep most of the transmitted light within the core, the refractive index of the core must be greater than refractive index of the clad. By narrowing the difference between refractive indices of the core and the clad, it is possible to increase the quantity of stray light going into the clad and to thus improve evanescent wave spectroscopy.

Since the theoretical attenuation of a chalcogenide fiber is about an order of magnitude lower than that of a fiber made of silica glass, the chalcogenide optic fiber sensor can be as long as needed. This possibility is not present with other materials, such as polycrystalline materials, where length of the fiber sensor may be limited by an unduly high attenuation due to scattering.

Both the core and the clad typically are made of chalcogenide glass, which is a vitreous material composed of the chalcogen elements of Group VI of the Periodic Table. These elements are usually mixed with elements of Groups IV and V to form the familiar compound glasses. More particularly, chalcogenide glasses are made from mixtures containing at least one of sulfur, selenium, and tellurium. Other elements can be added. Examples of other elements that can be combined with at least one chalcogen element include germanium, arsenic, and antimony. Particularly useful chalcogenide glass compositions, in atomic percent, include the following: $As_{20}S_{80}$, $Ge_{30}As_{40}S_{30}$, $As_{40}S_{60}$, $As_2Se_3$, $As_2SeTe_2$, $Ge_{10}As_{50}Te_{40}$, $Ge_{15}As_{10}Se_{75}$, $Ge_{28}As_{12}Se_{60}$, $GeSeTe$, $Ge_3P_3Te_{14}$, $Ge_2PTe_7$.

The use of chalcogenide fibers for remote chemical sensing is advantageous not only for wide transmittance range but also for chemical durability. Although chalcogenide glass cannot be used in strongly basic enviroments because it undergoes chemical attack, there are numerous environments where chalcogenide fibers can be used. For instance, chalcogenide glass does not react with water, unlike fluoride glass, and can, therefore, be used in aqueous environments. Additionally, chalcogenide glass can be used in acidic and organic environments.

Although the clad is typically made of a chalcogenide glass, it can be made of another glass, if desired. The clad can be made from chalcohalide glasses which are prepared from mixtures of halide and chalcogenide glass components. Halide glasses have relatively poor chemical durability and a low glass transition temperatures, especially the non-fluoride glasses, whereas chalcogenide glasses are well known for their chemical durability but their relatively high refractive indices give rise to high reflectivities from the glass surface. Chalcohalides have some beneficial characteristics of both glasses. The structural aspect of these glasses is interesting from a fundamental viewpoint since chalcogenide glasses are predominantly covalent and halide glasses are predominantly ionic in character.

At a desired location along a chalcogenide fiber, as at about the midpoint thereof, there is at least one unclad region coated with a polymeric material, with a different polymeric material in each region. The unclad region is typically 0.1–25 centimeters, more typically 1–10 cm long longitudinally along the fiber, but can be longer if improved sensitivity is desired. If there is more than one region, the spacing between the regions can be from a minimum which does not create detection interference from adjacent regions to a maximum dictated by practical considerations such as minimum bending radius and length of the fiber. The minimum bending radius for chalcogenide fibers that are circular in cross-section and have core-clad diameters on the order of about 200 microns, is on the order of about 1 cm. In a typical arrangement, the spacing between adjacent regions will be in the range of about 0.1–25 cm, more typically 1–10 cm.

The polymeric material is disposed in each unclad region on the fiber in the form of a sleeve. The thickness of the polymeric material is typically less than the thickness of the clad so that it is typically disposed below the level of the clad although it can extend above the clad, if it is so desired. The refractive index of the polymeric material is below the refractive index of the clad or the core, which means that the polymeric material behaves as a clad. Typically, the refractive index of the polymeric material is about 1.2–1.6. Although the polymeric material can be hydrophobic or hydrophilic, typically it is hydrophobic. A hydrophobic polymeric material in an aqueous environment containing a hydrophobic analyte will repel water but will preferably solubilize and concentrate the hydrophobic analyte.

To be suitable for use herein, the polymeric material should have an attraction or affinity for the chemical tested so that within a short period of time, such as a period of 10 minutes or less, typically 1 minute or less, and more typically less than about 10 seconds, the polymeric material can concentrate the chemical or chemicals to be tested in order to yield a reliable real time analysis. Some polymeric materials have enrichment ratios of in excess of 100 times. This means that a polymeric material with an enrichment of 100 will have a concentration of a chemical that is 100 times concentration of that chemical in the surrounding medium.

Specific examples of suitable polymeric materials include low density polyethylene (LDPE) and polydimethylsiloxane (PDMS). LDPE polymeric material can be used to detect chlorinated hydrocarbons whereas PDMS polymeric material can be used to detect benzene, toluene and/or xylene.

One region on the chalcogenide optic fiber, coated with LDPE can be used to detect one or more chlorinated hydrocarbons and another region on the fiber, coated with PDMS, can be used to detect any one or more of benzene, toluene, and xylene. If a region is coated with a mixture of LDPE and PDMS polymeric materials, then such a mixture can be used to detect one or more chlorinated hydrocarbons and one or more of benzene, toluene and xylene. Since the most common undesirable chemical contaminats, especially in drinking water, include chloroform, methylene chloride, trichlorethylene, benzene, toluene, and xylene, LDPE and PDMS polymeric materials in separate regions or deposited as a mixture in a single region should suffice for most purposes.

If more than one chlorinated hydrocarbon is present in a solution, then the presence and concentration of the chlorinated hydrocarbons can be detected by a region coated with LDPE. A spectrometer will indicate presence of all chlorinated hydrocarbons present in the solution. It is not necessary to provide a separate region for testing a single or a limited number of chemicals. This same practice applies to a region coated with PDMS.

FIG. 1 is a schematic representation of some of the characteristic vibrational signatures or absorption bands of various molecular species. It is possible to identify a compound by reference to FIG. 1 or a similar figure and/or the complete vibration pattern for that compound available in the literature. The analyte must possess a dipole to interact with infrared light and give rise to an absorption spectrum.

Figure 2:
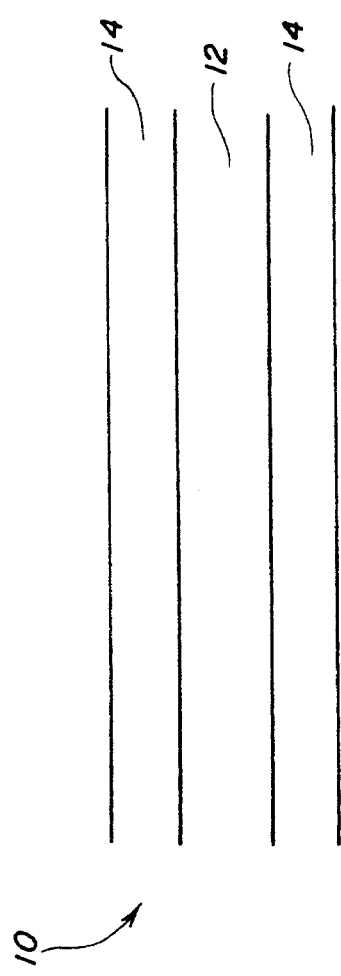
FIG. 2 is a schematic representation of a cross-section of a cylindrical chalcogenide fiber comprising a core and a clad which surrounds the core.

Chalcogenide optical fiber 10 shown in FIG. 2 in axial cross-section includes chalcogenide cylindrical core 12 and tubular chalcogenide clad 14. The clad wraps around the core but it can be a segment on the core. The clad is in the form of a continuous sleeve around the core. The refractive index of chalcogenide core 12 is about 2.8 and that of the chalcogenide clad is also about 2.8 but is lower than that of the core in order to maintain substantially all of the light transmitted through the fiber within the core. Some of the light from the core enters the clad and this light can be used for chemical detection by evanescent wave spectroscopy.

Optical fiber 10 can be made by any method typically used to make clad fibers. For example, either the double crucible method or the rod-in-tube method may be used. In a preferred embodiment, the optical fiber is made by the double crucible method. In this preferred embodiment, the fibers can be drawn at about 350° C.–450° C. at a rate of about 0.5–10 m/min, depending on the fiber diameter.

Figure 3:
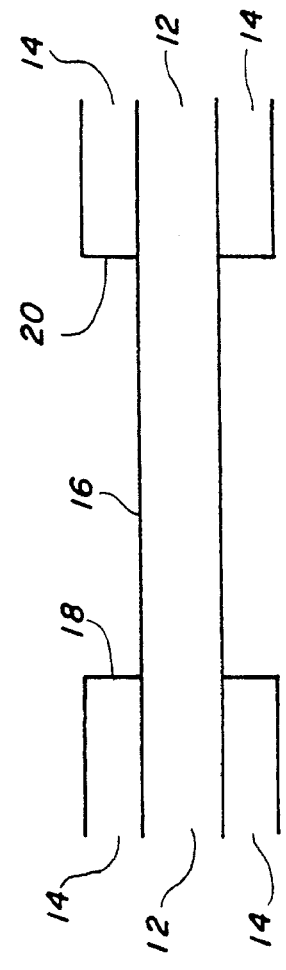
FIG. 3 is a schematic representation of a cross-section of a cylindrical fiber comprising a core, a clad, and an unclad region.

Region 16 is shown in FIG. 3 extending from the edges 18 and 20 of the circumferential clad or sleeve 14 which surrounds core 12. Region 16 is unclad. Alternatively, region 16 may have a clad that extends into the core, i.e., the core in the region can be of a smaller radial extent than what is shown so that the combined radius of the core and clad in region 16 is no greater than the radius of the core outside that region.

The region is typically formed by chemically etching the optical fiber for a period long enough to remove the clad. Etching can be effected in a matter of seconds by immersing an optical fiber into an etching solution which is typically a solution of a strong alkali. Suitable example of etching solutions include sodium hydroxide, potassium hydroxide, lithium hydroxide, and the like. The stronger the etching solution the less time it will take to etch or dissolve the clad. The extent of etching can be controlled to remove all or part of the clad or any portion of the fiber core. The etching period is typically less than about one-half minute, more typically up to about 5 seconds.

Figure 4:
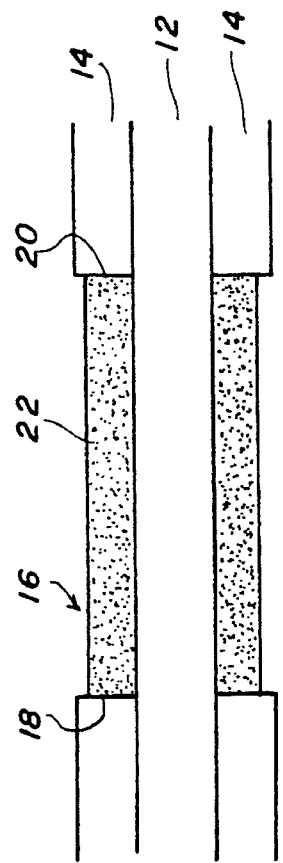
FIG. 4 is a schematic representation of a cross-section of a cylindrical fiber comprising a core and a clad, with an unclad region having a polymer thereon.

Polymer 22 is shown in FIG. 4 as disposed in region 16 between edges 18,20 of clad 14 disposed on core 12. Polymer 22 is in the form of a cylindrical sleeve whose thickness is typically less than the thickness of the clad. The polymer is typically hydrophobic and has the property of having affinity for the chemical to be detected.

The polymer, if in solid form, can be dissolved in a suitable solvent, for ease of application, and then applied to the region. If the polymer is in a liquid state, it can be diluted, if desired, and then applied to the region. Since an optical fiber is very thin, being up to about 500 microns in diameter, only a very small amount of the polymer is needed for application to the region. Although any manner can be used to apply the polymer to the region, one dependable way is to apply small drop of the polymer from a pipette to a region while holding the fiber essentially vertically so that the polymer drop runs down and coats the fiber.

Figure 5:
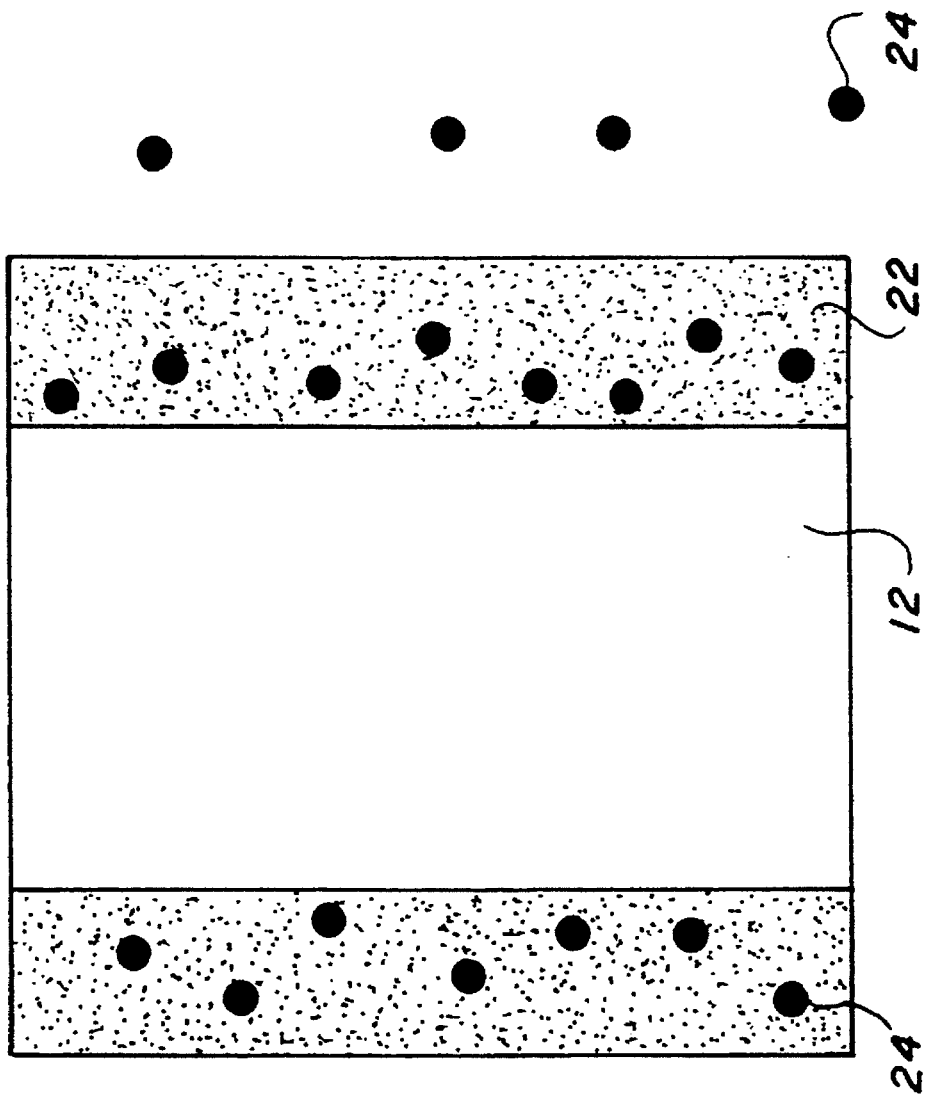
FIG. 5 illustrates an unclad region with a polymer sheeth around the core of the fiber, wherein the polymer concentrates chemical species found in the surrounding environment.

Chemical molecules 24 in FIG. 5 are shown within and outside polymer 22. The polymer is shown disposed on core 12. Chemical molecules 24 shown in FIG. 5. outside of polymer 22 can be disposed in a gaseous, liquid or solid medium although the medium is typically liquid, such as a polluted body of water. Chemical molecules 24 in FIG. 5 within polymer 22, are molecules which have been drawn into the polymer and concentrated therein by the affinity of the polymer for the chemical molecules 24.

Figure 6:
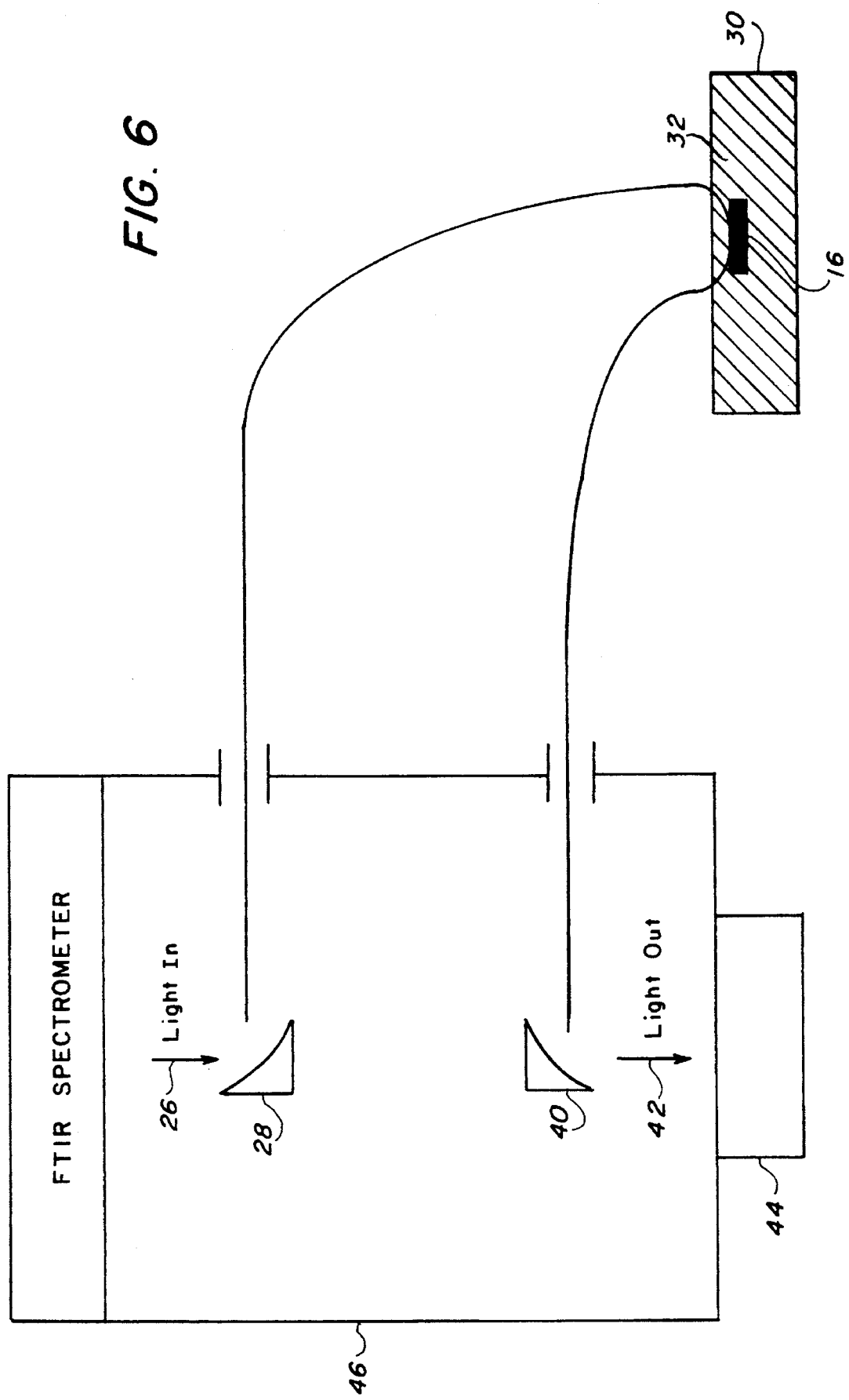
FIG. 6 is a schematic representation of a chalcogenide chemical sensor for remote spectroscopy according to an embodiment of the present invention.

FIG. 6 is a schematic representation of the sensor setup of an embodiment of this invention. This set up shows light from a light source along path 26 being introduced into optical fiber 10 by means of parabolic mirror 28. Fiber 10 passes through sensor cell 30. One or more of regions 16 with polymer in it are disposed in the section of the fiber which is in the sensor cell. Medium or sample 32 is disposed in the sensor cell. The sample can be a stationary or flowing body. Light emitted from the distal end of the optical fiber is reflected by means of mirror 40 into path 42 which enters detector 44.

The light that is introduced into the fiber can come from any light source. Typically, it is monochromatic light from a laser or a broadband light from a glow bar or a filament, which can be provided within a spectrometer 46. Detector 44 can also be a part of the spectrometer.

The operation of the chemical sensor will now be described in connection with the embodiment shown in FIG. 6 although it should be understood that the chemical sensor can be used in different embodiments. In the embodiment of FIG. 6, one end of optical fiber 10 is shown disposed in spectrometer 46 where light along the path of arrow 26 is directed at the parabolic mirror 28 which directs the light into fiber 10. Light typically comes from broadband glow bar source, not shown, within spectrometer 46. Fiber 10 loops through sensor cell 30. The distal end of fiber 10 disposed in spectrometer 46 emits light at parabolic mirror 40. Parabolic mirror 40 directs the light emitted from fiber 10 into detector 44, where the light is analyzed. Medium 32, typically an aqueous solution, is disposed in the sensor cell 30 and is either stationary in the sensor cell or is flowed therethrough continuously. A stationary medium is shown in FIG. 5. The chemical sensor can detect presence and concentration of one or more chemicals in the medium to a sub ppm level.

Fiber 10 has at least one region 16 devoid of clad and coated with polymer 22, as shown in FIG. 3, which region is disposed in the sensor cell 30. Disposition of the region and enrichment of the chemical by the polymer within the sensor cell facilitates evanescent wave spectroscopy.

Evanescent wave spectroscopy relies on light waves which propagate through the core of an optical fiber and extend fractionally beyond the extremity of the core. Since what is outside of the core is typically a clad having a lower refractive index than that of the core, the light wave that goes beyond the core is re-directed by the clad inwardly and the light wave is thus propagated through the fiber core until it reaches the opposite end of the fiber.

If, however, a portion of the clad is replaced with a polymer, and that polymer has an affinity for one or more chemicals in the medium, the polymer concentrates the chemicals and thus facilities their detection. Any light that goes beyond the core and is not absorbed by an analyte is re-directed by the polymer back into the core. This light, when detected by a spectrometer, yields spectrometric absorption bands of the chemicals present in the polymer. Since the intensity of absorption in the absorption bands is directly proportional to the concentration of the chemicals in the medium, the actual concentration of the chemicals in the medium can be obtained. Determination of chemicals in this manner provides a nearly instantaneous result.

Although FIG. 6 illustrates the use of a sensor cell, it should be understood that the chemical sensor described herein can be used at a dumpsite or on a body of water to yield real time analysis of potentially toxic or carcinogenic chemicals.

The threshold detection of the chemical fiber optic sensor described herein can be reduced in several ways, including increasing the length of the polymer-coated region, using a polymer with a high enrichment factor, reducing the cross-sectional area of the core, bending the fiber, and reducing the difference between refractive indices of the core and the polymer. By increasing length of the polymer-coated region, a greater interaction area is made available for evanescent wave spectroscopy, which will enhance determination of a chemical. Lower detection limits are also attainable by using polymers with high enrichment factors, exceeding, for example, 100. With more molecules of a chemical within the polymer sleeve, a better determination thereof can be made. By reducing cross-sectional area of the core within the region, more light is introduced into the polymer on the core, which results in an enhanced analysis. Bending a fiber also introduces more light into the polymer on the core in the polymer-coated region, which also results in a lower detection limit. Finally, a lower detection limit can be attained by better matching or reducing the refractive index differential between the core and the polymer on the core. This variant can yield only limited reduction in the detection limit since the refractive index of a chalcogenide glass is typically about 2.8 and the refractive indices of the polymer are typically below 2.

The invention having been generally described, the following examples are given as particular embodiments of the invention to demonstrate the practice and advantages thereof. It is understood that the examples are given by way of illustration and are not intended to limit the specification or the claims that follow in any manner.

EXAMPLE 1

This example demonstrates the use of a fiber optic sensor according to the present invention in a saturated solution of benzene in water, using about two meters of a chalcogenide glass fiber with polydimethylsiloxane (PDMS) in the polymer-coated region on the fiber.

The core-clad fiber was 180 microns in diameter with a core 120 microns in diameter. The composition of the core was $Ge_{30}As_{10}Se_{30}Te_{30}$ in atomic percent and that of the cladding was $Ge_{25}As_{12}Se_{40}Te_{23}$, also in atomic percent. The refractive index of the core was about 2.8 and that of the clad was about 2.78. The numerical aperture of the fiber was 0.35. The fiber had a UV-cured acrylate coating.

This fiber had one region that was formed by removing the protective acrylate with concentrated sulfuric acid and then etching the clad glass. The etching operation was carried out by immersing the fiber in 45% by weight potassium hydroxide solution for two seconds, which removed all of the clad in one region. The width of the region was about 3 cm. The removal of the clad during etching was monitored using an FTIR spectrometer.

After the clad was etched, the fiber was removed from the solution and dried by blowing dry air. The highly viscous PDMS polymer was applied to the etched region using a pipette with the fiber disposed vertically. The thickness of the dried polymer on the core was about 100 microns. Refractive index of the polymer was about 1.4.

At this point, the baseline reference spectrum was recorded by the FTIR spectrometer with air surrounding the region.

A schematic representation of the sensing system for detecting benzene in water is shown in FIG. 6. The region was at the midpoint of the fiber about 3 cm in width along the fiber axis with the PDMS polymer disposed on the core. The PDMS polymer is hydrophobic and has a strong affinity for benzene.

The region was then immersed in the benzene-water solution. As soon as the region on the fiber was immersed in the solution, the absorption peaks due to the presence of benzene became immediately discernible. The intensity of the bands grew quickly with time and equilibrium or concentration was fully attained in about 30 seconds after immersion. The fiber was then pulled out of the solution. The absorption bands due to benzene decreased in intensity immediately and were completely gone in about 20 seconds. The difference between equilibration period after fiber immersion and decay after fiber removal can be attributed to the high volatilization rate of benzene in air compared to that in solution. The concentration of benzene in the water tested with this sensor was on the order of a few hundred ppm.

With the set-up of this example, the minimum detection limit is estimated to be about 20 ppm.

EXAMPLE 2

This example demonstrates fiber optic analysis of an aqueous solution saturated with benzene and trichloroethylene using about two meters of a chalcogenide glass fiber having two polymer-clad regions at about the mid-point of the fiber, one region coated with polydimethylsiloxane (PDMS) and the other region coated with low density polyethylene (LDPE).

The core-clad fiber of this experiment was 180 microns in diameter with a core about 120 microns in diameter. The composition of the core in atomic percent was $Ge_{30}As_{10}Se_{30}Te_{30}$ and that of the clad was $Ge_{25}As_{12}Se_{40}Te_{23}$, on the same basis. The refractive index of the core was about 2.8 and that of the clad was about 2.78. The numerical aperture of the fiber was 0.35. The fiber had a UV-cured acrylate coating.

This fiber had two regions at about the mid-point thereof formed by removing the protective acrylate coating with concentrated sulfuric acid and then etching the clad glass. The etching operation was carried out by immersing the fiber in 45% by weight potassium hydroxide solution at two different locations on the fiber for two seconds each time to completely remove the clad. The width of each etched section was about 3 cm and the etched sections were spaced about 25 cm apart.

After the clad was etched, the fiber was removed from the solution and air dried. Although the PDMS polymer was highly viscous, the LPDE polymer was in a solid, granular form which was dissolved in 20 ml of toluene for ease of application. The polymers in liquid form were applied to the etched sections using a pipette and applying the PDMS polymer to the first etched section and the LPDE polymer to the second etched section. The polymers were applied sequentially by holding the fiber vertically and applying a drop of the polymer at the upper extremity of the etched section so that the drop descended along the fiber core as it coated the core. The thickness of the dried polymers was about 100 microns in each case. The refractive index of the PDMS polymer was about 1.4 and that of the LPDE polymer was about 1.5.

At this point, a baseline reference spectrum was recorded for the fiber sensor in air prior to immersion in the liquds.

A schematic representation of the sensing system for detecting benzene and trichloroethylene in water is shown in FIG. 6, except that two regions were immersed in the solution not one, as shown. The PDMS polymer is hydrophobic and has strong affinity for benzene and none for trichloroethylene. The LDPE polymer is also hydrophobic but it has an affinity for trichloroethylene and none for benzene.

The two regions on the fiber were then immersed in the aqueous solution of benzene and trichloroethylene. As soon as the regions were immersed in the solution, the absorption peaks due to the presence on benzene and trichloroethylene became immediately discernible. The intensity of the bands grew quickly with time and equilibrated or stabilized in 30 seconds after immersion. The fiber was then pulled out of the solution and the absorption bands due to benzene and trichloroethylene decreased in intensity immediately and were completely gone in about 20 seconds. The difference between the equilibration period after fiber immersion and decay after fiber withdrawal can be attributed to the high volatilization rate of benzene and trichloroethylene in air compared to that in solution. The concentration of benzene and trichloroethylene in water tested by this sensor was a few hundred ppm and a few hundred ppm, respectively, calibrated to a standard. The concentration of benzene and trichloroethylene obtained with this sensor coincided with the known concentrations of these two chemicals in the water.

The minimum detection limit of the sensor in this example was estimated to be about 10 ppm.

Many modifications and variations of the present invention are possible in light of the above teachings. It is therefore to be understood that within the scope of the appended claims, the invention may be practiced otherwise than as specifically disclosed.

What is claimed is:

1. A fiber optic sensor comprising a fiber;
   said fiber comprising a core and a clad having a lower refractive index than that of said core, said clad being in contact with said core;
   said fiber also comprising at least one region which is partially or totally unclad;
   a polymer disposed in said at least one region, said polymer having a lower refractive index than that of said core;
   said core being made of glass containing an element selected from the group consisting of sulfur, selenium, tellurium, polonium, and mixtures thereof.

2. The fiber sensor of claim 1 wherein the diameter of said fiber core and clad is about 20–500 microns; the diameter of said core is about 10–90% of the total diameter of said core and clad; and said core is made of glass containing an element selected from the group consisting of sulfur, selenium, tellurium, and mixtures thereof.

3. The fiber sensor of claim 2 wherein said clad is glass comprising an element selected from the group consisting of sulfur, selenium, tellurium, and mixtures thereof.

4. The fiber sensor of claim 3 wherein the longitudinal extent of said at least one region is about 0.1–25 cm and said clad envelopes said core.

5. The fiber sensor of claim 3 wherein the diameter of said core is about 30–70% of the total diameter of said core and clad; and longitudinal extent of said at least one region is about 0.1–25 cm.

6. The fiber sensor of claim 5 wherein said at least one region is completely devoid of said clad, said polymer is disposed over said core in the form of a sleeve, and said fiber comprising two or more of said regions.

7. The fiber sensor of claim 6 wherein each of said at least one regions is in the range of 0.1–25 cm in longitudinal extent along said fiber, each of said at least one regions is spaced from each other, and a different polymer is disposed in each of said at least one regions.

8. The fiber sensor of claim 7 including means for generating a light signal, means for introducing the light signal into said fiber, and means for directing the light signal from said fiber into a detector.

9. The fiber sensor of claim 8 wherein said means for generating a light signal is a broadband source, said means for introducing the light into said fiber and said means for directing the light source from said fiber is at least one mirror, and said means for detecting spectra of chemicals in said polymers is a Fourier transform infrared spectrometer.

10. The fiber sensor of claim 9 wherein said polymer on one of said regions is polydimethylsiloxane and said polymer in another of said regions is low density polyethylene.

11. The fiber sensor of claim 9 wherein each of said at least one regions includes a polymer coating disposed around and in contact with said core, each of said polymers being hydrophobic and distinct from any other polymer disposed on said fiber.

12. A fiber sensor for sensing at least one chemical having minimum detection limit below the ppm level comprising a fiber;
   said fiber comprising a core and a clad having a lower refractive index than said core, said clad enveloping and being in contact with said core;
   said fiber also comprising at least one region which is unclad;
   a polymer coating in said at least one region having lower refractive index than said core;
   said core and said clad being made of glass comprising an element selected from the group consisting of sulfur, selenium, tellurium, polonium, and mixtures thereof.

13. The fiber sensor of claim 12 wherein the diameter of said fiber core and clad is about 20–500 microns; the diameter of said core is in the range of about 10–90% of the total diameter of said core and clad; and said core and said clad being made of glass comprising an element selected from the group consisting of sulfur, selenium, tellurium, and mixtures thereof.

14. The fiber sensor of claim 13 wherein the longitudinal extent of said unclad region is about 0.1–25 cm.

15. The fiber sensor of claim 14 wherein the diameter of said core is about 30–70% of the total diameter of said core and clad.

16. The fiber sensor of claim 15 wherein said unclad region is completely unclad; said polymer is disposed over said core in the form of a sleeve; one of said at least one region has a coating of polydimethylsiloxane and another one of said at least region region has a coating of low density polyethylene.

17. The fiber sensor of claim 16 wherein each of said unclad regions is about 0.1–25 cm in longitudinal extent along said fiber; said regions are spaced apart from each other; and a different polymer is coated in each of said regions.

18. The fiber sensor of claim 17 including means for generating a light signal; means for introducing the light signal into said fiber; means for directing the light signal from said fiber into a detector; and means for detecting chemicals in said polymers.

19. The fiber sensor of claim 18 wherein said means for generating a light signal is a broadband source; said means for introducing the light into said fiber and said means for directing the light source from said fiber is at least one mirror; and said means for detecting chemicals in said polymers is a Fourier transform infrared spectrometer.

20. The fiber sensor of claim 19 wherein each of said unclad regions includes a polymer in sleeve form disposed around and in contact with said core; each of said polymers being hydrophobic and distinct from any other polymer disposed on said fiber.

* * * * *